US012745954B2

(12) United States Patent
Lee et al.

(10) Patent No.: US 12,745,954 B2
(45) Date of Patent: Sep. 29, 2026

(54) OBSTRUCTIVE SLEEP APNEA SYNDROME DIAGNOSIS METHOD USING MACHINE LEARNING

(71) Applicant: INDUSTRY-ACADEMIC COOPERATION FOUNDATION, YONSEI UNIVERSITY, Seoul (KR)

(72) Inventors: Joon Sang Lee, Seoul (KR); Hyung Ju Cho, Seoul (KR); Yoon Jeong Choi, Seoul (KR); Hwi Dong Jung, Seoul (KR); Susie Ryu, Seoul (KR)

(73) Assignee: Industry-Academic Cooperation Foundation, Yonsei University, Seoul (KR)

( * ) Notice: Subject to any disclaimer, the term of this patent is extended or adjusted under 35 U.S.C. 154(b) by 286 days.

(21) Appl. No.: 16/933,915

(22) Filed: Jul. 20, 2020

(65) Prior Publication Data

US 2021/0219908 A1 Jul. 22, 2021

(30) Foreign Application Priority Data

Jan. 17, 2020 (KR) ........................ 10-2020-0006700

(51) Int. Cl.
*A61B 5/00* (2006.01)
*A61B 5/021* (2006.01)
(Continued)

(52) U.S. Cl.
CPC ............ *A61B 5/4818* (2013.01); *A61B 5/021* (2013.01); *A61B 5/087* (2013.01); *A61B 5/107* (2013.01); *A61B 5/7267* (2013.01); *A61B 6/032* (2013.01)

(58) Field of Classification Search
CPC ....... A61B 5/4818; A61B 5/021; A61B 5/087; A61B 5/107; A61B 5/7267; A61B 6/032;
(Continued)

(56) References Cited

U.S. PATENT DOCUMENTS

| | | | | |
|---|---|---|---|---|
| 11,723,614 B2 * | 8/2023 | Hu | ........................... | A61B 6/50 600/407 |
| 2008/0146893 A1 * | 6/2008 | Levendowski | ...... | A61B 5/0002 600/300 |

(Continued)

FOREIGN PATENT DOCUMENTS

| | | |
|---|---|---|
| JP | 2018011770 A | 1/2018 |
| KR | 101958561 B1 | 3/2019 |

(Continued)

OTHER PUBLICATIONS

Sang Lee, Joon et al. Computational analysis of airflow dynamics for predicting collapsible sites in the upper airways: machine learning approach . Journal of Applied Physiology. https://journals.physiology.org/doi/full/10.1152/japplphysiol.01033.2018?rfr_dat=cr_pub++0pubmed&url_ver=Z39.88-2003&rf (Year: 2019).*

(Continued)

*Primary Examiner* — Allen Porter
*Assistant Examiner* — Moussa Haddad
(74) *Attorney, Agent, or Firm* — BROADVIEW IP LAW, PC

(57) ABSTRACT

Provided is an obstructive sleep apnea syndrome diagnosis method using machine learning. An embodiment of the present invention is directed to providing an obstructive sleep apnea syndrome diagnosis method using machine learning, which diagnoses obstructive sleep apnea syndrome by extracting parameters related to obstructive sleep apnea syndrome from a geometrical shape of an airway and performing machine learning using data calculated through simulation. Another embodiment of the present invention is directed to providing an obstructive sleep apnea syndrome diagnosis method using machine learning, which improves accuracy of diagnosis of obstructive sleep apnea syndrome and proposes a quantitative standard by diagnosing the
(Continued)

obstructive sleep apnea syndrome from the geometrical shape of the airway as described above.

5 Claims, 8 Drawing Sheets

(51) Int. Cl.
*A61B 5/087* (2006.01)
*A61B 5/107* (2006.01)
*A61B 6/03* (2006.01)

(58) Field of Classification Search
CPC ....... A61B 5/7275; A61B 5/7264; A61B 6/52; G16H 50/50; G16H 30/20; G16H 50/20; G06N 20/00
See application file for complete search history.

(56) References Cited

U.S. PATENT DOCUMENTS

| | | | | |
|---|---|---|---|---|
| 2016/0110632 | A1* | 4/2016 | Kiraly | G06V 10/267 382/128 |
| 2017/0329927 | A1* | 11/2017 | Taherian | A61B 6/50 |
| 2019/0117151 | A1* | 4/2019 | Stern | G16H 20/40 |
| 2022/0222823 | A1* | 7/2022 | Bafkar | G16H 30/40 |

FOREIGN PATENT DOCUMENTS

| | | | | |
|---|---|---|---|---|
| KR | 20190114386 A | | 10/2019 | |
| WO | WO-2012035538 A1 | * | 3/2012 | A61B 5/08 |

OTHER PUBLICATIONS

Cisonni, Julien et al. Numerical simulation of pharyngeal airflow applied to obstructive sleep apnea: effect of the nasal cavity in anatomically accurate airway models . Med Biol Eng Comput. URL: https://pubmed.ncbi.nlm.nih.gov/26429351/ (Year: 2015).*

Lee, Dongwook et al. New High-order Methods using Gaussian Processes for Computational Fluid Dynamics Simulations . Journal of Physics:Conf. Series . URL: chrome-extension://efaidnbmnnnibpcajpcglclefindmkaj/https://iopscience.iop.org/article/10.1088/1742-6596/837/1/ (Year: 2017).*

Dong et al. "Simulation Study on Characteristics of the Vortex Structure in Human Mouth-throat Model in Cyclic Respiratory Pattern" Energy Procedia 17 ( 2012 ) 1786-1792 (Year: 2012).*

Yamamoto et al. "Mechanisms Underlying Improvement in Obstructive Sleep Apnea Syndrome by Uvulopalatopharyngoplasty", Case Rep Otolaryngol. 2017; 2017: 2120165. (Year: 2017).*

Kim, S. et al., "Obstructive Sleep Apnea Diagnosis Using Machine Learning Models: Survey and Open Challenges," The Korean Institute of Information Scientists and Engineering, Jun. 2019, 5 pages. (Submitted with English Machine Translation of Abstract).

Korean Intellectual Property Office, Office Action Issued in Application No. 2020-0006700, Jan. 28, 2022, 15 pages.

Yeom, S. et al., "Computational analysis of airflow dynamics for predicting collapsible sites in the upper airways: machine learning approach," Journal of Applied Physiology. vol. 127, No. 4, Oct. 2019, Available Online Jul. 18, 2019, 15 pages.

Lee, J. et al., "Computational Fluid Dynamics and machine learning analysis for bio-airflow dynamics," KSMTE, vol. 184, May 2019, 2 pages.

Ryu, S. et al., "Computational analysis of airflow dynamics for predicting collapsible sites in the upper airways: Advanced machine learning," Proceedings of the 15th Asian Symposium on Visualization (ASV15), Sep. 25, 2019, Busan, Korean, 1 page.

Ryu, S. et al., "Computational analysis of airflow dynamics for predicting collapsible sites in the upper airways: Advanced machine learning," Proceedings of the 72nd Annual Meeting of the APS Division of Fluid Dynamics, Nov. 23, 2019, Seattle, Washington, 2 pages. (Submitted with English Abstract).

Ryu, S. et al., "Computational analysis of airflow dynamic for predicting Obstructive sleep apnea syndrome: Advanced machine learning," Biomedical Engineering Society for Circulation, vol. 26, Dec. 7, 2019, 3 pages. (Submitted with English Abstract).

* cited by examiner

OBSTRUCTIVE SLEEP APNEA SYNDROME DIAGNOSIS METHOD USING MACHINE LEARNING

CROSS-REFERENCE TO RELATED APPLICATION

The present application claims priority to Korean Patent Application No. 10-2020-0006700 filed on Jan. 17, 2020. The entire contents of the above-listed application is hereby incorporated by reference for all purposes.

TECHNICAL FIELD

The following disclosure relates to an obstructive sleep apnea syndrome diagnosis method, and in particular, to an obstructive sleep apnea syndrome diagnosis method using machine learning, which provides an accurate diagnosis and quantitative standard for obstructive sleep apnea syndrome using machine learning.

BACKGROUND AND SUMMARY

Obstructive sleep apnea syndrome (OSAS), a general obstructive sleep apnea syndrome disorder, refers to a syndrome of apnea or hypopnea that occurs as an area of an upper airway (from the nasal cavity to the pharynx, which is referred to as "airway" hereinafter) is closed or narrowed during sleep. Most OSAS patients suffer from excessive snoring during sleep and OSAS is quite common as statistics show that one in six adults is reported to suffer from OSAS. Patients with OSAS tend to have a high prevalence of diseases such as cardiovascular disease, and thus patients requiring examination or treatment have increased.

In general, polysomnography is performed to diagnose current obstructive sleep apnea syndrome. Polysomnography measures brain waves, oxygen saturation, breathing, sleep posture, pulse, and thoracic movements of a patient at the same time, and is the most essential diagnostic test for diagnosing obstructive sleep apnea syndrome. However, in order to perform polysomnography, a large number of skin-attached sensors (e.g., Korean Patent Publication No. 2019-0114386 ("Biometric Information Detecting Sensor", 2019 Oct. 10) need to be attached to a face, a head, and the like, and in the case of the chest and abdomen, the sensors are to be worn around and bound on the chest and abdomen. As such, a state where the large number of sensors are attached to and worn around the patient causes significant inconvenience to the patient. In other words, since the patient is placed in a completely different environment from a normal sleeping environment, the test results are incorrect in many cases. In addition, since polysomnography should be performed while the patient is sleeping for at least 6 hours or more at night, the number of tests that may be performed per day is also limited.

In order to solve this problem, various attempts have been made to diagnose obstructive sleep apnea syndrome through a simpler test. As an example, Korean Patent Registration No. 1958561 ("Obstructive Sleep Apnea Syndrome Diagnosis Device and Operation Method Thereof, 2019.03.08, which is referred to as "related art document" hereinafter) discloses a technique of calculating obstructive sleep apnea syndrome based on a patient's skull structure information. More specifically, it is a technique of obtaining a probability of obstructive sleep apnea syndrome using statistical formulas elicited from the related art document regarding a magnitude of snoring sound, a waist measurement, a distance from a subnasale to a stomion, a thickness of uvula, and an age. In fact, however, an organ where a major syndrome appears in the occurrence of obstructive sleep apnea syndrome is the airway as described above, but in the related art document, only the statistical probability is obtained through the shape or structure of the periphery, substantially without considering the shape or structure of the airway at all, thus making it difficult to expect to obtain quantitatively accurate diagnosis results.

RELATED ART DOCUMENT

Patent Document

1. Korean Patent Laid-open Publication No. 2019-0114386 ("Biometric Information Detecting Sensor", 2019 Oct. 10.)
2. Korean Patent Registration No. 1958561 ("Obstructive Sleep Apnea Syndrome Diagnosis Device and Operation Method Thereof", 2019 Mar. 8).

DISCLOSURE

Technical Problem

An embodiment of the present invention is directed to providing an obstructive sleep apnea syndrome diagnosis method using machine learning, which diagnoses obstructive sleep apnea syndrome by extracting parameters related to obstructive sleep apnea syndrome from a geometrical shape of an airway and performing machine learning using data calculated through simulation.

Another embodiment of the present invention is directed to providing an obstructive sleep apnea syndrome diagnosis method using machine learning, which improves accuracy of diagnosis of obstructive sleep apnea syndrome and proposes a quantitative standard by diagnosing the obstructive sleep apnea syndrome from the geometrical shape of the airway as described above.

Technical Solution

In one general aspect, an obstructive sleep apnea syndrome diagnosis method using machine learning includes: an information elicitation operation of eliciting flow characteristic information using an information elicitation machine learning model from airway shape information of an airway of a subject; and a symptom diagnosis operation of eliciting symptom status information indicating whether the subject has an obstructive sleep apnea syndrome symptom (OSAS) using a symptom diagnosis machine learning model from the flow characteristic information elicited in the information elicitation operation and biological characteristic information of the subject.

The information elicitation operation may include information elicitation preparation operation of constructing the information elicitation machine learning model using the airway shape information of the airway and flow characteristic information elicited through computational fluid dynamics (CFD), for a plurality of airways previously selected for training; and an information elicitation management operation of eliciting flow characteristics information using the information elicitation machine learning model constructed in the information elicitation preparation operation from the airway shape information of the airway for at least one airway newly selected for analysis, wherein only the information elicitation preparation operation is performed until the information elicitation machine learning model is constructed and only the information elicitation management operation may be performed after the information elicitation machine learning model is constructed.

The information elicitation preparation operation may include a training airway shape information elicitation operation of eliciting airway shape information of the airway 3D modeled from a tomogram of the airway, for the plurality of airways previously selected for training; a training flow characteristic information elicitation operation of eliciting flow characteristic information through CFD by applying a boundary condition to the 3D model of the airway; and an information elicitation machine learning model constructing operation of constructing the information elicitation machine learning model by performing machine learning using a plurality of the airway shape information and flow characteristic information.

In the information elicitation machine learning model construction operation, the information elicitation machine learning model may be constructed by performing machine learning by a Gaussian process regression (GPR) algorithm or a multi-variate Gaussian process regression (MV-GP) algorithm.

The airway shape information may be at least one selected from among a length of the airway, a position of each of a plurality of points spaced apart from each other in a longitudinal direction of the airway, a diameter of a longer axis at each point, a diameter of a shorter axis at each point, a cross-sectional area at each point, and a minimum cross-sectional area.

The boundary condition may be at least one selected from among a pressure at an inlet or outlet position of the airway, a flow rate at the inlet or outlet position of the airway, and an adhesion condition of an inner wall of the airway.

The flow characteristic information may be at least one selected from among velocity, pressure gradient, swirling strength, pressure, airway resistance, deformation, vorticity, helicity, surface swirling strength, surface pressure gradient, wall shear stress, and surface pressure.

The information elicitation management operation may include: airway shape information elicitation operation of eliciting airway shape information of the airway 3D modeled from a tomogram of the airway, for at least one airway newly selected for an analysis purpose; and flow characteristic information elicitation operation of outputting flow characteristic information by inputting the airway shape information to the information elicitation machine learning model.

The symptom diagnosis operation may include: a symptom diagnosis preparation operation of constructing a symptom diagnosis machine learning model by performing machine learning using the flow characteristic information of the airway elicited in the information elicitation operation, biological characteristic information of the subject having the airway, and symptom status information of the subject, for a plurality of airways previously selected for training among the airways used in the information elicitation operation; and a symptom diagnosis management operation of outputting the symptom status information of the subject by inputting the flow characteristic information of the airway and the biological characteristic information of the subject having the airway to the symptom diagnosis machine learning model constructed in the symptom diagnosis preparation operation, for at least one airway newly selected for an analysis purpose, wherein only the symptom diagnosis preparation operation is performed until the symptom diagnosis machine learning model is constructed and only the symptom diagnosis management operation is performed after the symptom diagnosis machine learning model is constructed.

In the symptom diagnosis preparation operation, the symptom diagnosis machine learning model may be constructed by performing machine learning by a support vector machine (SVM) algorithm.

The biological characteristic information may be at least one selected from among an age, a BMI index, and a hypertension index.

Advantageous Effects

According to the present invention, the use of the geometrical shape of the airway in diagnosing the obstructive sleep apnea syndrome symptom (OSAS) may resolve various problems such as causing patient discomfort, lowering accuracy of diagnosis results, limiting diagnosis performance, and the like due to polysomnography which is conducted while a subject is actually sleeping with numerous sensors attached and worn in the related art. More specifically, according to the present invention, The OSAS is diagnosed by extracting parameters related to obstructive sleep apnea syndrome from the geometrical shape of the airway and performing machine learning using data calculated through simulation. That is, according to the present invention, the most direct diagnosis results may be obtained by performing diagnosis using the shape and the structure of the airway in which the obstructive sleep apnea syndrome symptoms are actually predominant and a relation of hydrodynamic characteristics in the airway, thereby ultimately significantly improving the accuracy of diagnosing whether the subject has the OSAS.

In addition, according to the present invention, by performing machine learning through the GPR algorithm using simulation data in predicting the flow characteristics of the airway, a calculation time may be significantly shortened by tens of thousands of times or more, compared to the case of using computational fluid dynamics (CFD). In addition, according to the present invention, by diagnosing obstructive sleep apnea syndrome using the SVM algorithm, a quantitative standard for patient classification may be provided and classification results may be rapidly provided.

DETAILED DESCRIPTION

Hereinafter, obstructive sleep apnea syndrome diagnosis method using machine learning according to the present invention having the configuration as described above will be described in detail with reference to the accompanying drawings.

Figure 1:
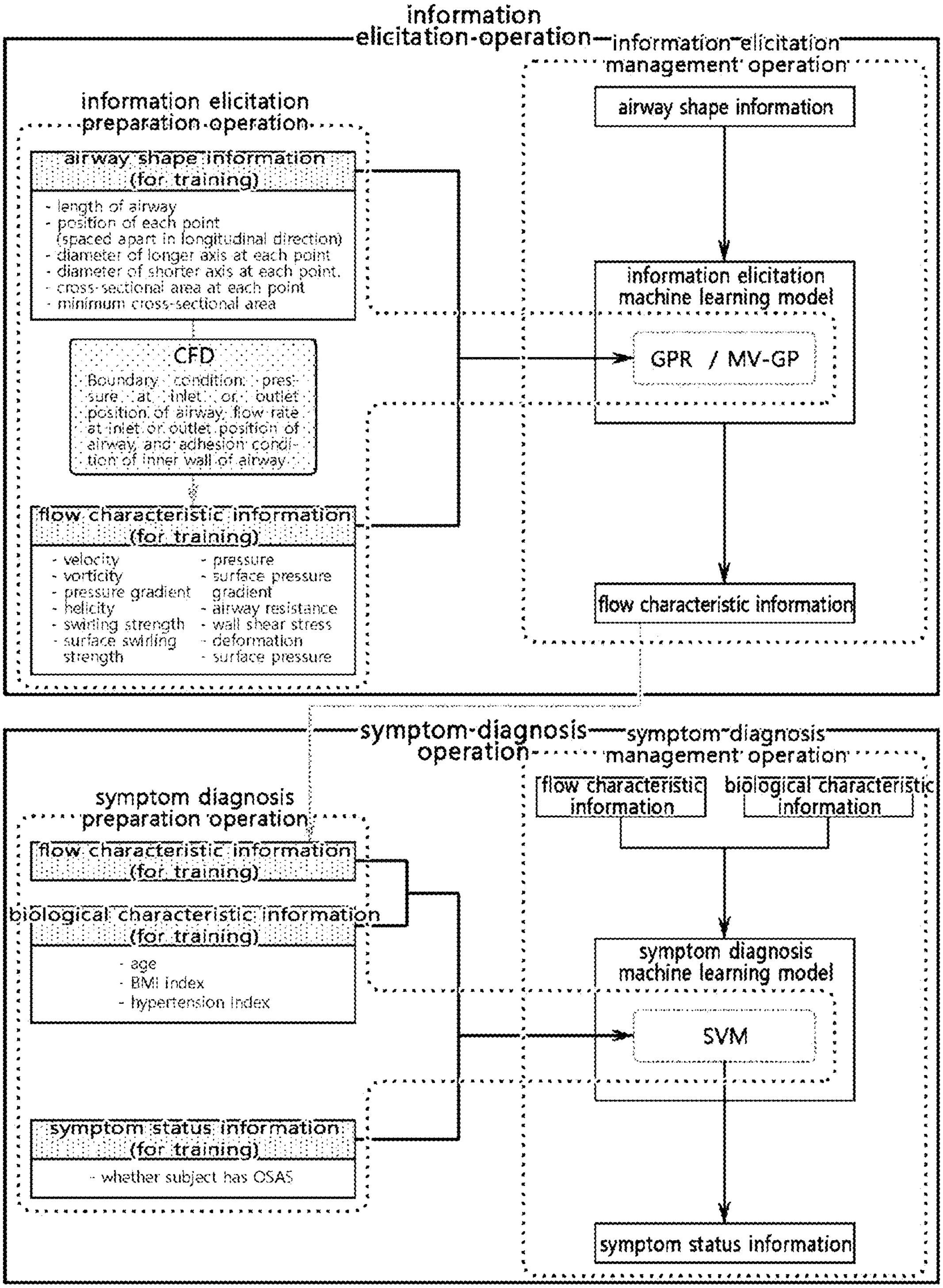
FIG. 1 is a block diagram of an obstructive sleep apnea syndrome diagnosis method of the present invention.

FIG. 1 is a view showing a configuration of an obstructive sleep apnea syndrome diagnosis method of the present invention. As shown in FIG. 1, the obstructive sleep apnea syndrome diagnosis method according to the present invention includes two operations: an information elicitation operation and a symptom diagnosis operation. In the information elicitation operation, flow characteristic information is elicited from airway shape information of an airway of a subject using an information elicitation machine learning model, and in the symptom diagnosis operation, symptom status information indicating whether the subject has an OSAS using a symptom diagnosis machine learning model from the flow characteristic information elicited in the information elicitation operation and biological characteristic information of the subject.

Polysomnography, which has been conventionally performed to diagnose obstructive sleep apnea syndrome, was inconvenient, inaccurate, and limited in performance due to a fundamental problem in which a subject had to sleep after numerous sensors are attached to the subject. To solve this problem, various methods, such as measuring sound of snoring or measuring movement of facial muscles during sleep, have been attempted but these methods cannot be fundamental solutions because the premise that measurement is performed in a state where the subject is in sleep remains the same.

However, in the present invention, as described above, obstructive sleep apnea syndrome is diagnosed based on a shape of an airway of the subject who is to be diagnosed to have obstructive sleep apnea syndrome. That is, when the subject is diagnosed by the diagnosis method of the present invention, only CT imaging is required and there is no need to sleep. As described above, the diagnosis method of the present invention has a remarkable effect that eliminates the most fundamental problem of the related art diagnosis methods, that is, the problem that the "state where the subject is in sleep" is essential. Therefore, according to the present invention, numerous problems such as patient discomfort, deterioration of accuracy due to a change in a sleeping environment, a long inspection time, and wasted support manpower, and the like entailed as the related art diagnosis methods require a sleep state are fundamentally resolved.

In the present invention, as briefly described above, different machine learning is used in each of the information elicitation operation and the symptom diagnosis operation. Hereinafter, each operation of the obstructive sleep apnea syndrome diagnosis method of the present invention will be described in more detail.

[1] Information Elicitation Operation

In the obstructive sleep apnea syndrome diagnosis method of the present invention, in a first operation, airway shape information of a subject is obtained and information for diagnosis is extracted therefrom, and in a second operation, whether the subject has the OSAS is diagnosed using the information extracted in the first operation. The information elicitation operation is the first operation described above, that is, the process of extracting information for diagnosis from the airway shape information of the subject.

In the information elicitation operation, as described above, flow characteristic information is elicited from the airway shape information of the airway of the subject using an information elicitation machine learning model. The information elicitation operation includes specific operations of an information elicitation preparation operation and an information elicitation management operation as shown in FIG. 1. Until the information elicitation machine learning model is constructed, only the information elicitation preparation operation is performed, and after the information elicitation machine learning model is constructed, only the information elicitation management operation is performed. Each operation will be described in detail below.

The information elicitation preparation operation is, in short, a process in which the information elicitation machine learning model is constructed. In order to construct the information elicitation machine learning model, machine learning using airway shape information and flow characteristic information is required, and the flow characteristic information for training is obtained through computational fluid dynamics (CFD). In terms of operations, the information elicitation preparation operation may include a operation of eliciting shape information of an airway for training (or a training airway shape information elicitation operation), a operation of eliciting flow characteristic information for training (or a training flow characteristic information elicitation operation), and a operation of constructing an information elicitation machine learning model (or an information elicitation machine learning model construction operation).

Figure 2:
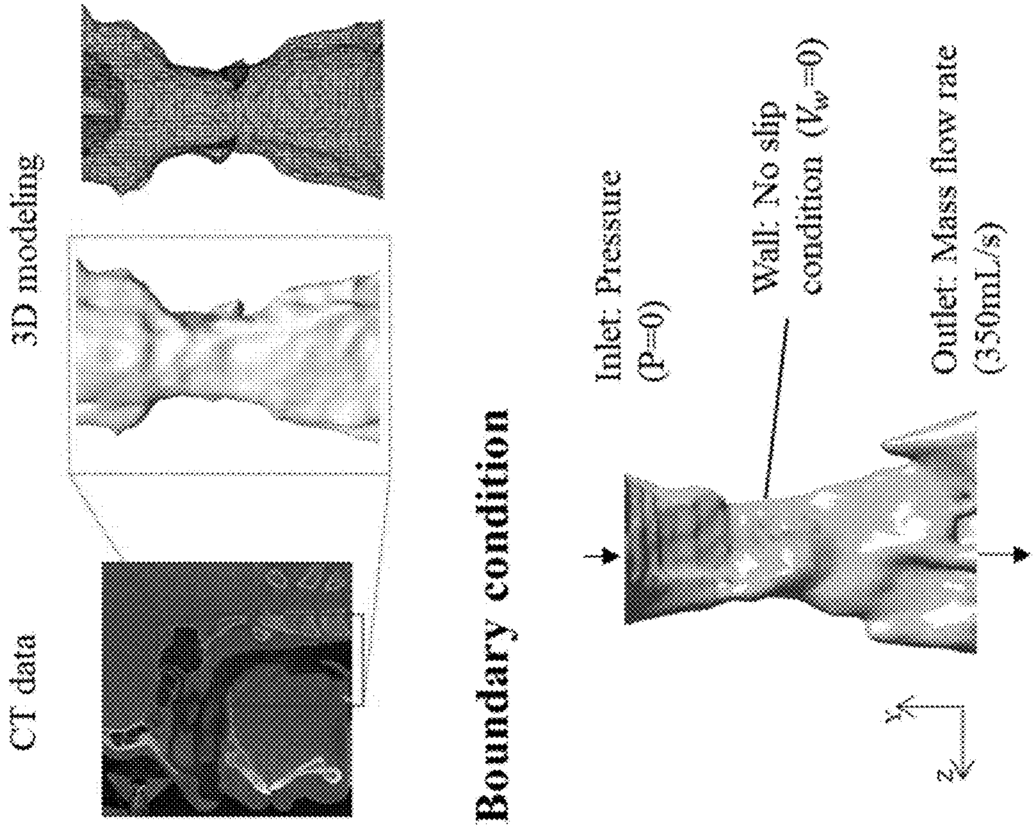
FIG. 2 shows an example of a process of eliciting flow characteristic information from airway shape information of an airway.

In the operation of eliciting the shape information of the airway for training, airway shape information of the airway 3D modeled from a tomogram of the airway is elicited for a plurality of airways previously selected for training. FIG. 2 shows an example of a process of eliciting flow characteristic information from the airway shape information of the airway. On an upper side of FIG. 2, an example of deriving a 3D model by 3D modeling an airway with CT data of the airway is shown. The airway shape information of the airway may be obtained from the 3D model of the airway created as described above, and here, the airway shape information may include a length of the airway, a position of each of a plurality of points spaced apart from each other in a longitudinal direction of the airway, a diameter of a longer axis at each point, a diameter of a shorter axis at each point, a cross-sectional area at each point, a minimum cross-sectional area, and the like.

Figure 3:
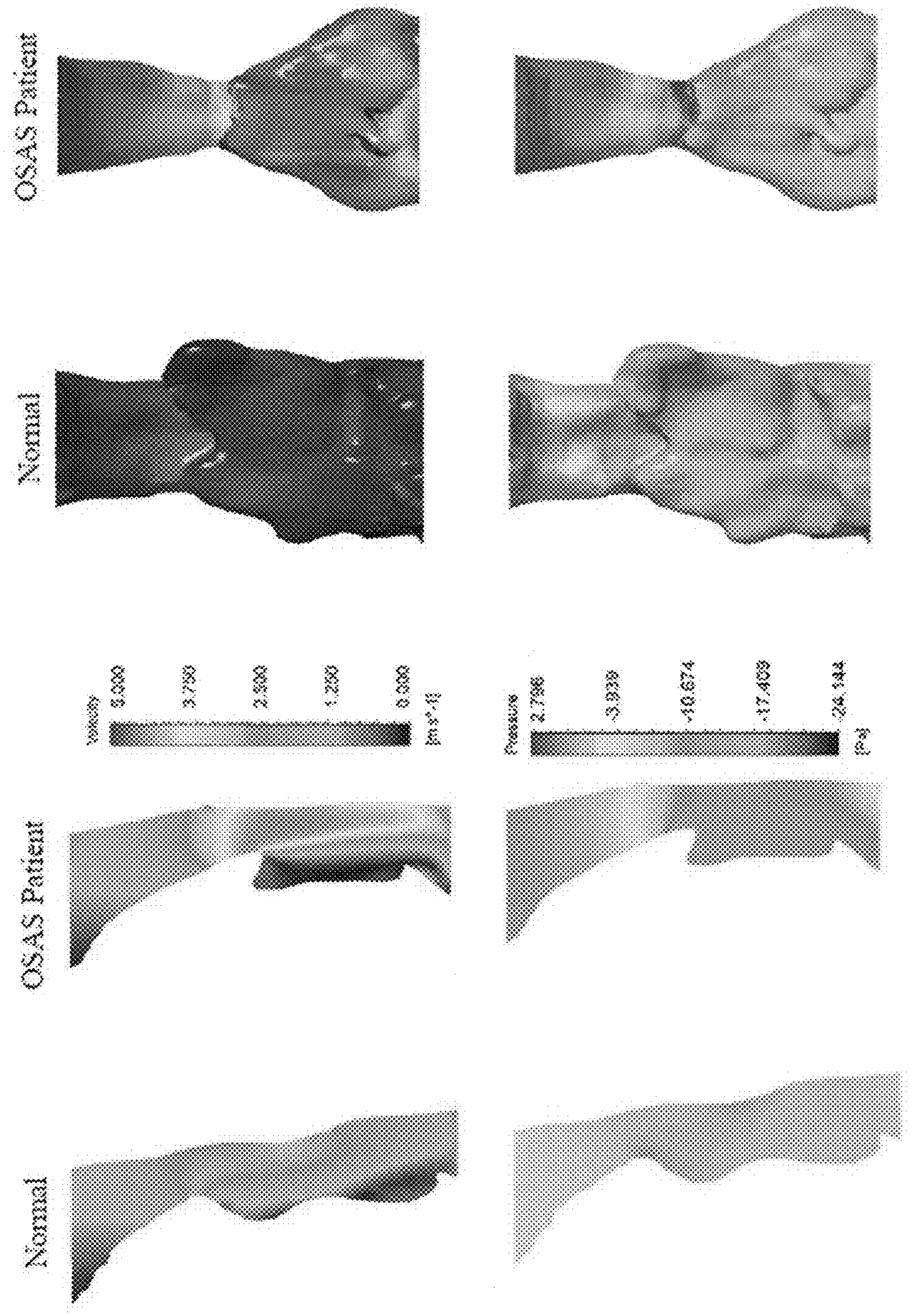
FIGS. 3 and 4 show an example of flow characteristics information results calculated using computational fluid dynamics (CFD).
Figure 4:
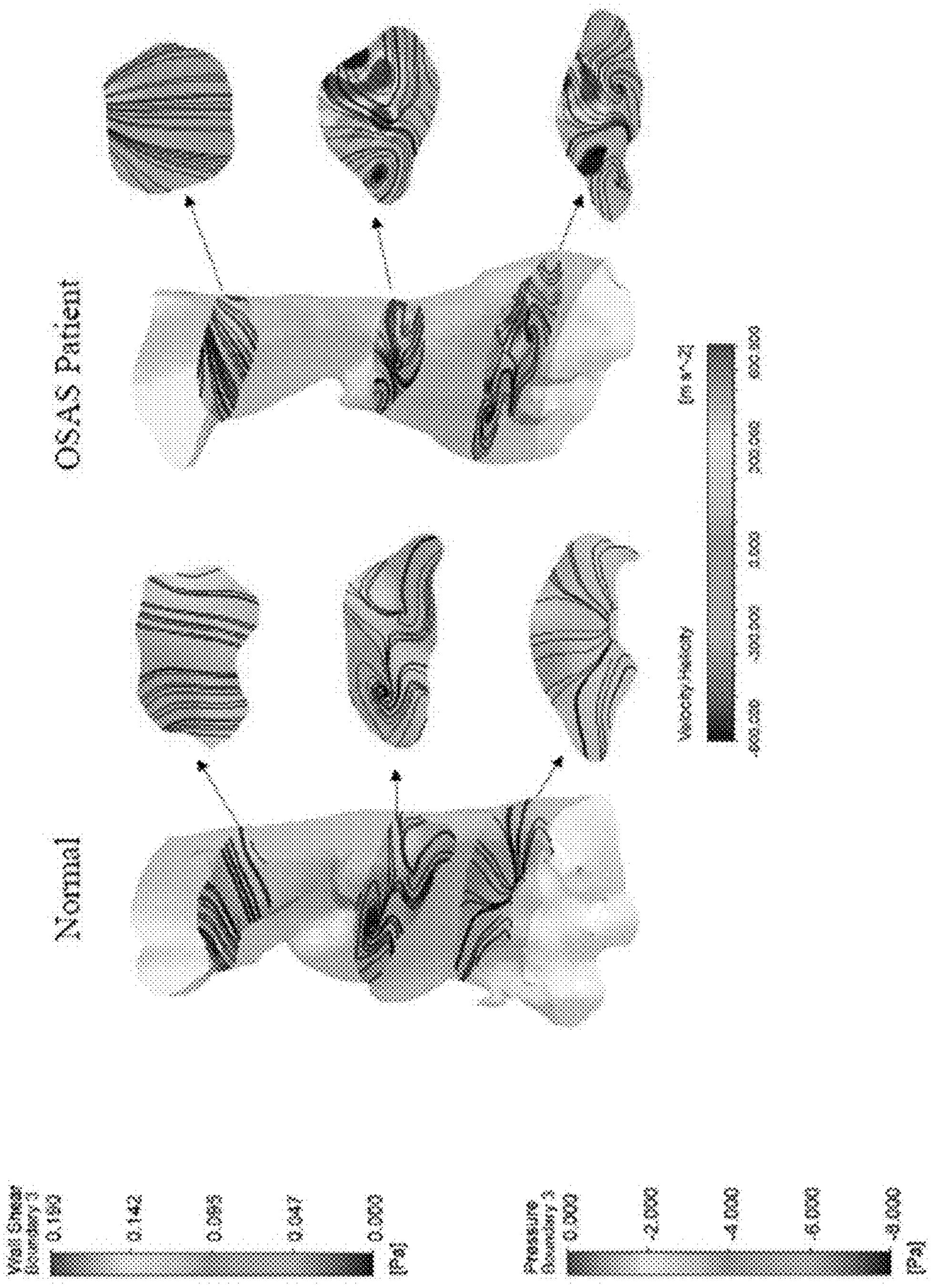

In the operation of eliciting flow characteristic information for training, flow characteristic information is elicited through CFD by giving boundary conditions to the 3D model of the airway. An example of giving boundary conditions is shown on a lower side of FIG. 2. Here, the boundary conditions may include a pressure at an inlet or outlet position of the airway, a flow rate at the inlet or outlet position of the airway, and an adhesion condition of an inner wall of the airway. Various flow characteristic information may be obtained by performing simulation using CFD by giving the boundary conditions. That is, flow characteristics of air passing through the airway may be known. Here, the flow characteristic information may be velocity, pressure gradient, swirling strength, pressure, airway resistance, deformation, vorticity, helicity, surface swirling strength, surface pressure gradient, wall shear stress, surface pressure, and the like. FIGS. 3 and 4 show an example of flow characteristic information results calculated using CFD.

In the operation of constructing an information elicitation machine learning model, the information elicitation machine learning model is constructed by performing machine learning using a plurality of the airway shape information and flow characteristic information. The information elicitation machine learning model is fundamentally devised to output flow characteristic information when airway shape information is input. Here, without training, accuracy is poor because there is insufficient basis to derive an output value from an input value, but the accuracy increases when machine learning is performed by matching airway shape information and flow characteristic information (accurately elicited through CFD actually) through the two operations of eliciting information for training described above and inputting the matched information. Of course, the accuracy may further increase as the matched set of the airway shape information/flow characteristic information is increasingly input.

In the present invention, in the operation of constructing the information elicitation machine learning model, machine learning may be performed by a Gaussian process regression (GPR) or multivariate Gaussian process regression (MV-GP) algorithm. As described above, in the present invention, the airway is divided into a plurality of portions and information such as a distance between each point, a cross-sectional area at each point, and the like is obtained as airway shape information of the 3D model of the airway, and information such as a flow rate, pressure, and the like at each point may be elicited as flow characteristic information.

The GPR or MV-GP algorithm itself is an algorithm widely known in the field of machine learning, so a detailed description thereof will be omitted, but a difference between the two algorithms is as follows. In the present invention, as described above, machine learning may be performed using either the GPR or MV-GP algorithm in the machine learning process, but the MV-GP algorithm is preferably used to further improve a speed and accuracy of calculation.

Figure 5:
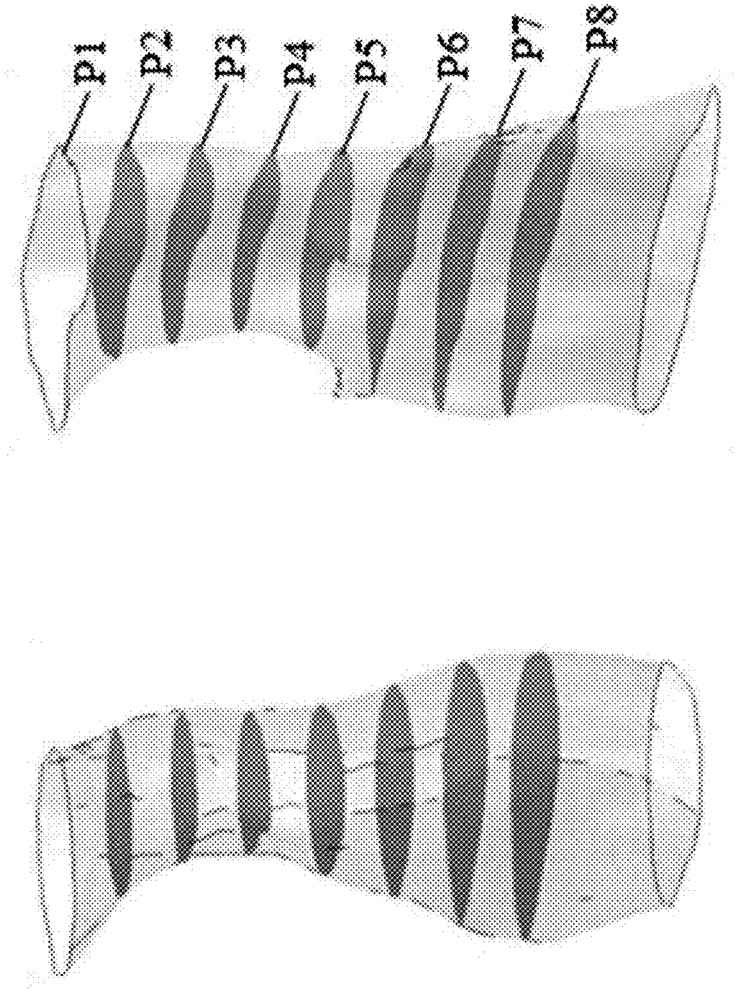
FIG. 5 shows various embodiments of a three-dimensional (3D) model of an airway.

FIG. 5 shows various embodiments of a 3D model of the airway. In the embodiment shown in FIG. 5, eight points are designated along a longitudinal direction of the airway. In the case of GPR, several response variables are independently considered, without considering a correlation between variables as an algorithm used when training a single response variable. Therefore, machine learning is performed on each of points P1, P2, . . . , P8 shown in FIG. 5, and a correlation between positions of each point or a correlation between flow characteristics (response variable) of each point is not considered. In contrast, in the case of MV-GP, machine learning is performed on all of the points P1, P2, . . . , P8, and thus training is performed by considering the correlation between positions of each point, and a correlation between flow characteristics.

In addition, in the case of GPR, since it is necessary to generate a prediction algorithm for each of the flow characteristic factors for each position of the airway, for example, 12 algorithms are required to be generated to predict 12 flow characteristic values, and in order to obtain a flow characteristic value for 8 points, a total of 12×8=96 operations are required. In contrast, in the case of MV-GP, when airway shape information is given by one algorithm, 12 flow characteristic values for each point may be obtained at once. Therefore, from the viewpoint of future automation and data processing, the MV-GP algorithm is much more advantageous.

There are more reasons for the MV-GP to be more advantageous. Actual human breathing includes exhalation and inhalation and has flow conditions that change over time. Therefore, it is obvious that an algorithm capable of predicting time-series data will be suitable for substituting actual breathing conditions. Here, in the case of GPR, since only a single response variable may be predicted, prediction must be made by fixing a flow rate and time series data cannot be predicted. Therefore, it is essential to use MV-GP, which may be able to predict time-series data to predict a flow characteristic value in actual breathing conditions.

Finally, unlike GPR, it is very tricky to realize the MV-GP algorithm. In order to create the MV-GP algorithm configured in a high-dimensional vector form, covariance in a complex nonlinear form different from the GPR must be obtained and set to a kernel function. Therefore, in the case of the existing GPR, an algorithm may be easily created using a tool box of a commercial program, but the MV-GP needs to have a code of more than 500 lines by itself and a code for 9 functions to create an algorithm.

As such, the MV-GP has very high distinctiveness and superiority compared to GPR, and it is obvious to prefer to use MV-GP considering a correlation between positions at each point and a correlation between flow characteristics to predict a flow of obstructive sleep apnea syndrome.

The information elicitation management operation is, in short, a process in which information is directly elicited using the information elicitation machine learning model. By stages, the information elicitation management operation may include an airway shape information elicitation operation and a flow characteristic information elicitation operation.

In the airway shape information elicitation operation, for at least one airway newly selected for an analysis purpose, airway shape information of the airway 3D modeled from a tomogram of the airway is elicited. Practically, an actual operation itself is the same as the previous operation of eliciting airway shape information for training, and the airway shape information obtained in the operation of eliciting airway shape information for training may be re-used at this stage for time saving and accuracy testing.

In the operation of eliciting flow characteristic information, the airway shape information is input to the information elicitation machine learning model and the flow characteristic information is output. In the operation of eliciting the flow characteristic information for training, the flow characteristic information is elicited through CFD with the airway shape information, and actually, it takes a long time of about 4 to 5 hours per airway. However, once the information elicitation machine learning model is constructed by performing the information elicitation preparation operation, the airway shape information is input to the information elicitation machine learning model so that the time for the flow characteristic information to be output is remarkably reduced to about 0.5 seconds.

Figure 6:
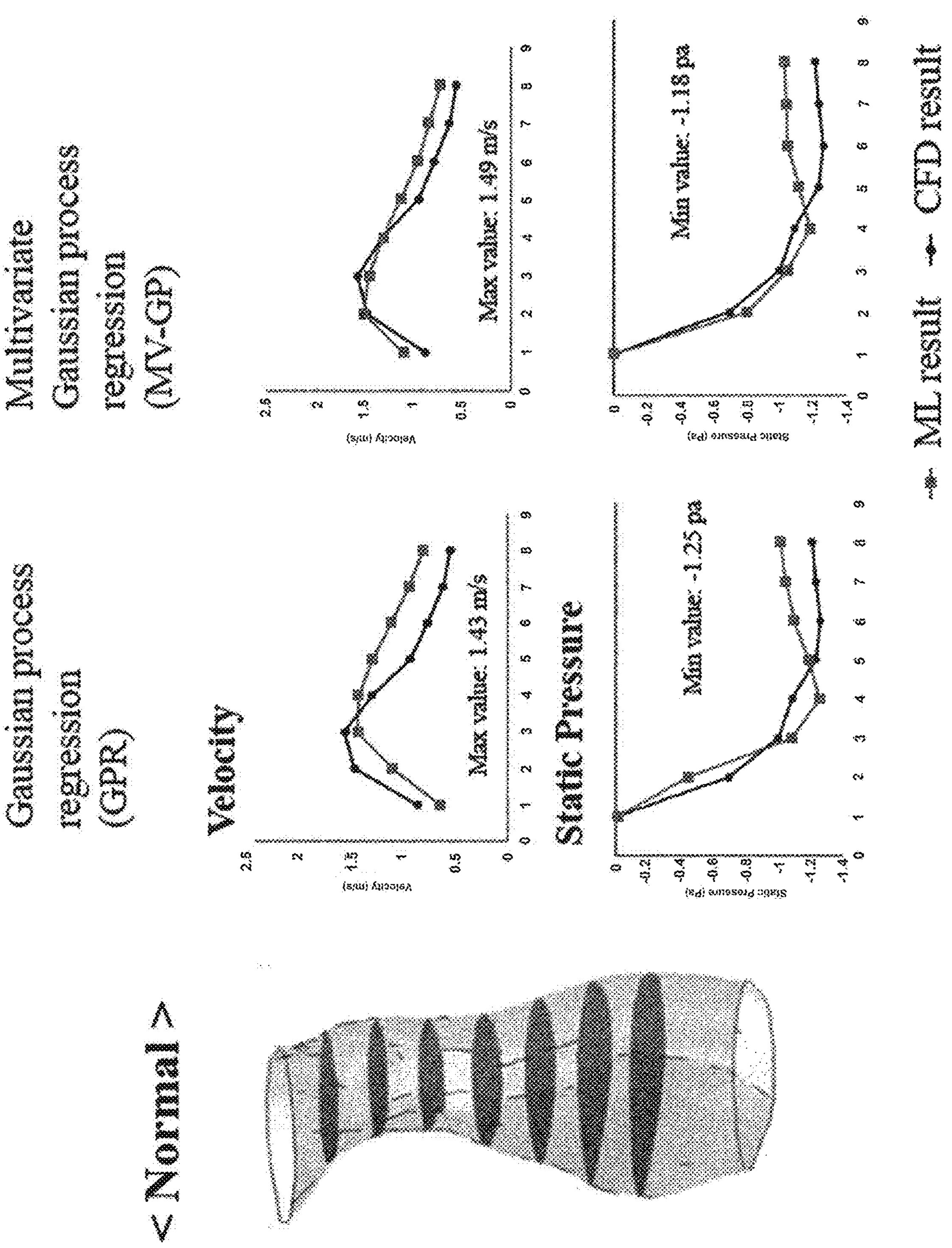
FIG. 6 shows examples of a 3D model of an airway of a normal subject, CFD interpretation results, and machine learning prediction results.
Figure 7:
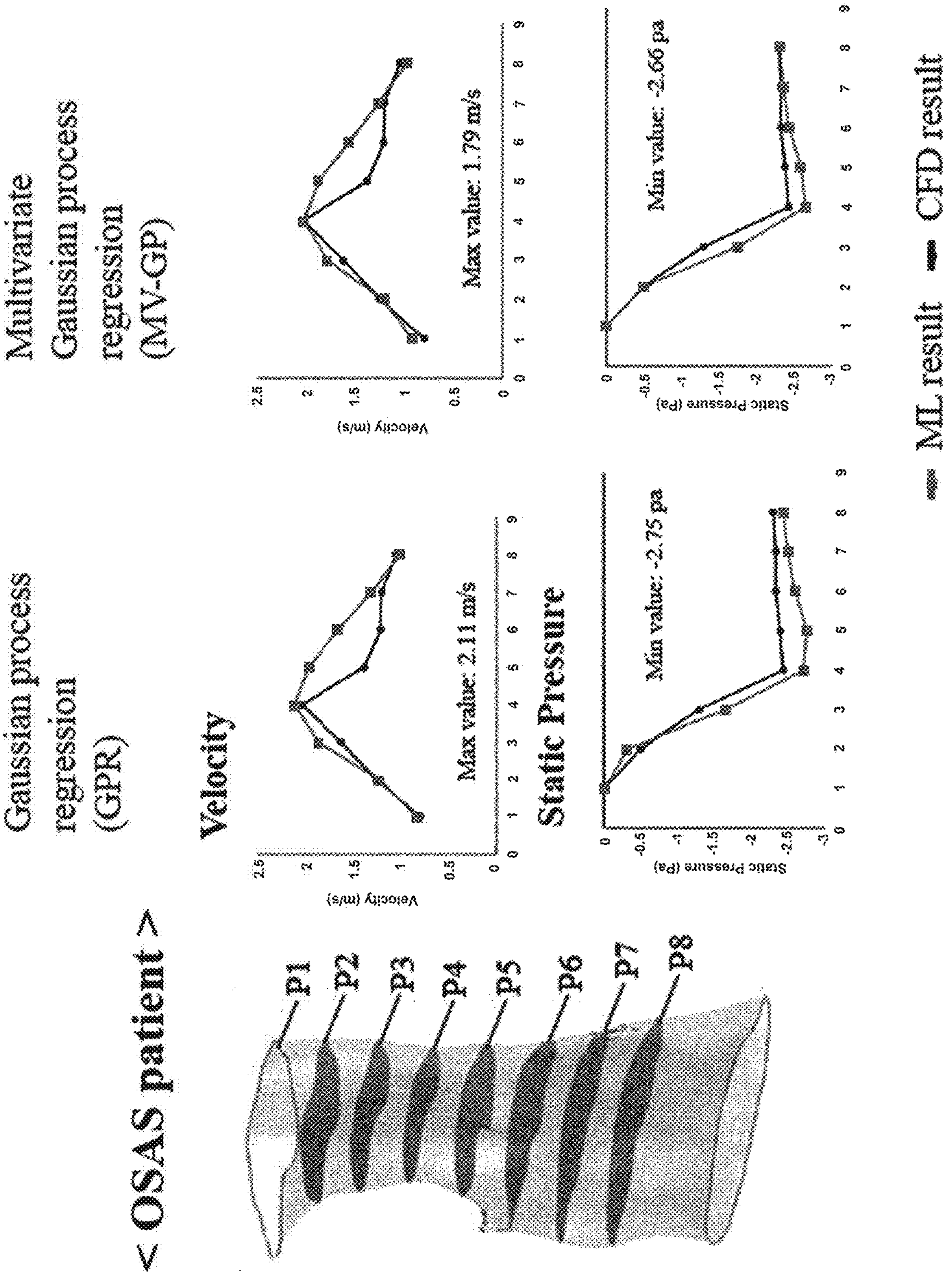
FIG. 7 shows examples of a 3D model of an airway of a subject who is a patient with a weak obstructive sleep apnea syndrome symptom, CFD interpretation results, and machine learning prediction results.

FIG. 6 shows examples of a 3D model of an airway of a normal subject, CFD interpretation results, and machine learning prediction results, and FIG. 7 shows examples of a 3D model of an airway of a subject who is a patient with a weak obstructive sleep apnea syndrome symptom, CFD interpretation results, and machine learning prediction results. In the examples of FIGS. 6 and 7, a 3D model of an airway is divided into 8 parts and analysis and prediction are performed as shown on the left. On the right side of FIGS. 6 and 7, interpretation results and prediction results of velocity and static pressure of air flowing through the airway are shown as graphs as flow characteristic information of each of the 8 parts. Since the interpretation results using CFD are exact values in itself, accuracy of the prediction results may be determined based on how close the prediction results using machine learning (ML) are to the interpretation results. Here, it can be seen that, as well shown in the graphs on the right side of FIGS. 6 and 7, in the case of using GPR or MV-GP, the prediction results are quite close to the interpretation results, and thus, the accuracy of the prediction results using the machine learning model is quite high.

Also, it can be seen that, comparing the left and right of the graph, MV-GP is more accurate than GPR. In fact, in an experiment conducted by the applicant, an average accuracy is confirmed to be about 72%.

[2] Symptom Diagnosis Operation

In the obstructive sleep apnea syndrome diagnosis method of the present invention, in a first operation, the airway shape information of the subject is obtained and information for diagnosis is extracted from the obtained airway shape information, and in a second operation, whether the subject has the OSAS is diagnosed using the information extracted in the first operation. The symptom diagnosis operation is a process of diagnosing obstructive sleep apnea syndrome from results of the second operation as the previous operation described above.

In the symptom diagnosis operation, as described above, symptom status information indicating whether the subject has the OSAS is elicited using a symptom diagnosis machine learning model from the flow characteristic information elicited in the information elicitation operation and biological characteristic information of the subject. The symptom diagnosis operation includes specific operations of a symptom diagnosis preparation operation and a symptom diagnosis management operation as shown in FIG. 1. Until the symptom diagnosis machine learning model is constructed, only the symptom diagnosis preparation operation is performed, and after the symptom diagnosis machine learning model is constructed, only the symptom diagnosis management operation is performed. Each operation will be described in detail below.

The symptom diagnosis preparation operation is, in short, a process of constructing the symptom diagnosis machine learning model. That is, in the symptom diagnosis preparation operation, the symptom diagnosis machine learning model is constructed by performing machine learning using the flow characteristic information of the airway elicited in the information elicitation operation, biological characteristic information of the subject having the airway, and symptom status information of the subject, for a plurality of airways previously selected for training among airways used in the information elicitation operation. Here, the biological characteristic information may be an age, a BMI index, a hypertension index, or the like. In general, a basic examination to measure age, height, weight, blood pressure, etc., and a urine test, blood test, etc. are performed while undergoing a medical examination in a hospital, and the bio-characteristic information may be easily obtained from test results.

The symptom diagnosis machine learning model is ultimately intended to cause symptom status information to be output when the flow characteristic information and the biological characteristic information are input. Similar to the process of constructing the information elicitation machine learning model described above, first, a proper input value/output value matching set should be put to be learned for machine learning, and here, it is obvious that more accuracy may be guaranteed using the accurate input value/output value secured in the previous information elicitation operation. For this reason, in the symptom diagnosis preparation operation, a machine learning model is constructed using the data previously used for training in the information elicitation operation.

In the present invention, in the symptom diagnosis preparation operation, machine learning may be performed by a support vector machine (SVM) algorithm. Since the SVM algorithm itself is a well-known algorithm in the field of machine learning, a detailed description thereof is omitted here.

The symptom diagnosis management operation is, in short, a process of directly diagnosing a symptom using the symptom diagnosis machine learning model. That is, in the symptom diagnosis management operation, for at least one newly selected airway for analysis, the flow characteristic information of the airway and biological characteristic information of the subject having the airway are input to the symptom diagnosis machine learning model constructed in the symptom diagnosis preparation operation, and symptom status information of the subject is output.

In the present invention, the subject to be diagnosed provides the biological characteristic information through the basic examination, and in addition, only CT imaging of the airway may be further performed. Then, airway shape information is first obtained from a CT photograph and flow characteristic information is elicited using the information elicitation machine learning model. When the obtained flow characteristic information and the biological characteristic information previously provided by the subject are combined and input to the symptom diagnosis machine learning model, symptom status information is output and obtained. As in the previous information elicitation operation, the prediction result using the machine learning model has a significantly short computation time. In other words, once the machine learning model is constructed and the constructed machine learning model has sufficient reliability, whether the subject has the OSAS may be rapidly and easily diagnosed with high accuracy using the machine learning model.

In particular, according to the present invention, it is possible to establish quantitative classification criteria when diagnosing symptoms. The SVM algorithm used in the symptom diagnosis machine learning model is used to classify information, and classification criteria are naturally created in the process of constructing the symptom diagnosis machine learning model. Thereafter, when actually performing symptom diagnosis by operating the symptom diagnosis machine learning model, an output value (symptom status information) is elicited using the quantitative classification criteria created when the model is constructed. That is, according to the present invention, obstructive sleep apnea syndrome is not diagnosed based on some qualitative criteria such as doctor's experience, knowledge, opinion, etc., but diagnosed based on the classification criteria established quantitatively in the machine learning model.

Figure 8:
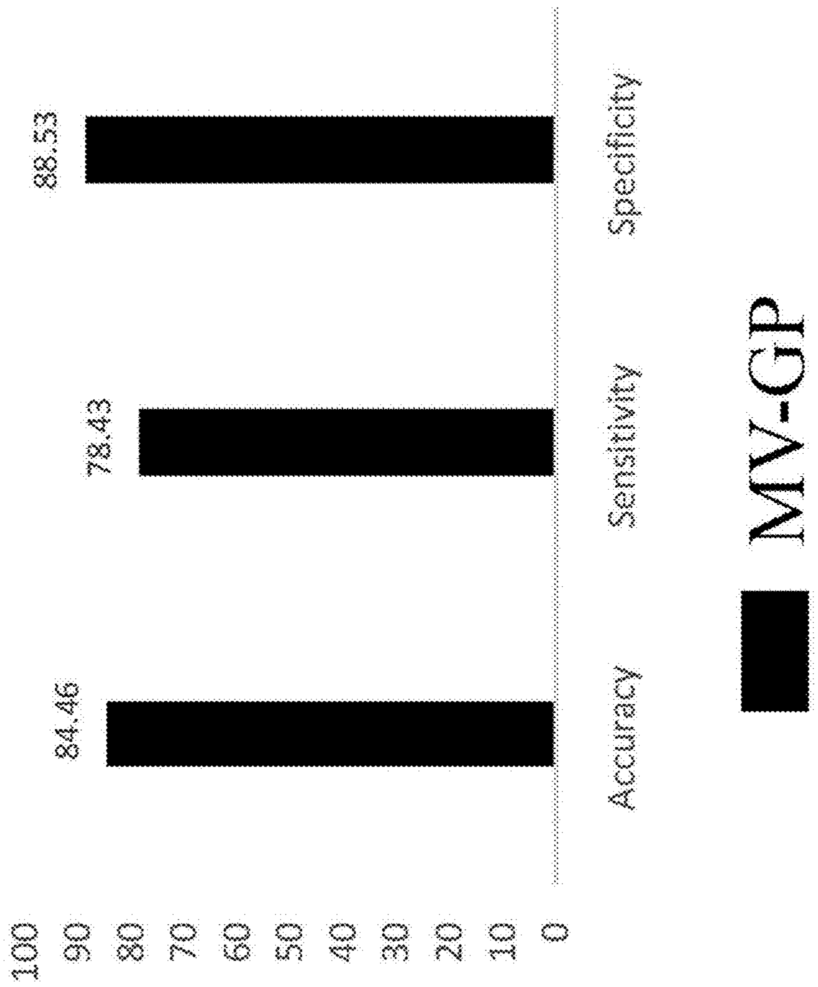
FIG. 8 shows a result of an obstructive sleep apnea syndrome diagnosis method of the present invention.

FIG. 8 shows accuracy results of an obstructive sleep apnea syndrome diagnosis method of the present invention, which is results when the MV-GP is used when constructing the information extracting machine learning model. As shown in FIG. 8, although slightly different depending on whether or not the obstructive sleep apnea syndrome diagnosis method of the present invention is used, both cases show very good results in which accuracy is about 85%, sensitivity is about 78%, and specificity is about 89%. In general, the accuracy of the results of the diagnosis of obstructive sleep apnea syndrome by a doctor in the clinical field is known to be about 80%. In fact, the accuracy of the results diagnosed using the machine learning model in the experiment conducted by the applicant is confirmed to be 80% or more on average. That is, it can be confirmed that the diagnosis by the machine learning model having the quantitative classification criteria according to the present invention has the same or better accuracy when compared with the qualitative determination of the doctor in the actual clinical field.

The present invention is not limited to the embodiment described above, the scope of application is varied, and those skilled in the art to which the present invention pertains may perform various modifications, without departing from the gist of the invention claimed in the claims.

The invention claimed is:

1. An obstructive sleep apnea syndrome diagnosis method using machine learning, the obstructive sleep apnea syndrome diagnosis method comprising:

an information elicitation operation of eliciting subject flow characteristic information using an information elicitation machine learning model from three-dimensional (3D) airway shape information of a subject airway; and a symptom diagnosis operation of eliciting symptom status information using a symptom diagnosis machine learning model from the flow characteristic information elicited in the information elicitation operation and biological characteristic information of the subject;

wherein the information elicitation operation comprises:

an information elicitation preparation operation of training the information elicitation machine learning model using training airway shape information of a training airway and training flow characteristic information elicited through computational fluid dynamics (CFD), for a plurality of training airways previously selected for training; and an information elicitation management operation of eliciting subject flow characteristics information, for at least one newly selected airway for analysis, using the information elicitation machine learning model trained in the information elicitation preparation operation from the plurality of training airways;

wherein the information elicitation preparation operation comprises:

a training airway shape information elicitation operation of creating, for each of the plurality of training airways previously selected for training, a 3D model of the training airway from a tomogram of the training airway and eliciting airway shape information of the training airway from the 3D model, for the plurality of training airways previously selected for training, wherein the training airway shape information comprises a length of the training airway, a position of each of a plurality of points spaced apart from each other in a longitudinal direction of the training airway, a diameter of a longer axis at each of the plurality of points, a second diameter of a shorter axis at each of the plurality of points, and a cross-sectional area at each of the plurality of points;

a training flow characteristic information elicitation operation of eliciting training flow characteristic information through performing a simulation using the CFD by applying a boundary condition to the 3D model of the training airway during the information elicitation preparation operation, wherein the boundary condition comprises a pressure at an inlet or an outlet position of the training airway and a flow rate at the inlet or the outlet position of the training airway, and wherein the flow characteristic information comprises velocity and pressure; and an information elicitation machine learning model training operation of training the information elicitation machine learning model by using the training airway shape information determined by the training airway shape information elicitation operation as an input parameter and the training flow characteristic information determined by the training flow characteristic information elicitation operation as an output parameter;

wherein the information elicitation management operation comprises:

a subject airway shape information elicitation operation of creating, for the at least one newly selected airway for analysis, a 3D model of the newly selected airway from a tomogram of the newly selected airway and eliciting airway shape information of the newly selected airway from the 3D model, for the at least one newly selected airway for analysis using the information elicitation machine learning model; and a subject flow characteristic information elicitation operation of outputting the subject flow characteristic information by inputting, into the information elicitation machine learning model, the subject airway shape information determined by the subject airway shape information elicitation operation;

wherein the information elicitation preparation operation is performed while the information elicitation machine learning model is trained, and the information elicitation management operation is performed after the information elicitation machine learning model is trained; and wherein the symptom diagnosis operation comprises:

a symptom diagnosis preparation operation of training the symptom diagnosis machine learning model by using the training flow characteristic information of the training airway elicited in the information elicitation operation and biological characteristic information of an individual having the training airway as input parameters, and symptom status information of the individual as an output parameter, for the plurality of training airways previously selected for training among the training airways used in the information elicitation operation, wherein the biological characteristic information comprises age and BMI; and a symptom diagnosis management operation of outputting the symptom status information of the subject by inputting the subject flow characteristic information of the subject airway determined from the information elicitation management operation and the biological characteristic information of the subject having the subject airway to the symptom diagnosis machine learning model trained in the symptom diagnosis preparation operation, for at least one second airway newly selected for analysis, wherein the symptom diagnosis preparation operation is performed while the symptom diagnosis machine learning model is trained, and the symptom diagnosis management operation is performed after the symptom diagnosis machine learning model is trained, and wherein the information elicitation machine learning model is trained by performing machine learning by adapting a Gaussian process regression (GPR) algorithm or adapting a multi-variate Gaussian process regression (MV-GP) algorithm during the information elicitation machine learning model training operation, and wherein the symptom diagnosis machine learning model is trained by performing machine learning by adapting a support vector machine (SVM) algorithm during the symptom diagnosis preparation operation.

2. The obstructive sleep apnea syndrome diagnosis method of claim 1, wherein the training airway shape information further comprises a minimum cross-sectional area.

3. The obstructive sleep apnea syndrome diagnosis method of claim 1, wherein the boundary condition further comprises an adhesion condition of an inner wall of the airway.

4. The obstructive sleep apnea syndrome diagnosis method of claim 1, wherein the training flow characteristic information further comprises pressure gradient, swirling strength, airway resistance, deformation, vorticity, helicity, surface swirling strength, surface pressure gradient, wall shear stress, and surface pressure.

5. The obstructive sleep apnea syndrome diagnosis method of claim 1, wherein the biological characteristic information further comprises hypertension index.

* * * * *